United States Patent [19]

Zajaczkowski

[11] Patent Number: 5,731,387
[45] Date of Patent: *Mar. 24, 1998

[54] IONICALLY-CROSSLINKED WATER-ABSORBENT GRAFT COPOLYMER

[75] Inventor: Michael J. Zajaczkowski, Yoe, Pa.

[73] Assignee: Adhesives Research, Inc., Glen Rock, Pa.

[*] Notice: The term of this patent shall not extend beyond the expiration date of Pat. No. 5,395,907 and 5,508,367.

[21] Appl. No.: 612,261

[22] Filed: Mar. 7, 1996

Related U.S. Application Data

[63] Continuation-in-part of Ser. No. 399,876, Mar. 7, 1995, Pat. No. 5,508,367, which is a continuation-in-part of Ser. No. 272,827, Jul. 11, 1994, Pat. No. 5,395,907.

[51] Int. Cl.⁶ ............................................. C08F 270/04
[52] U.S. Cl. ............................ 525/330.2; 525/326.9; 525/329.4; 526/320
[58] Field of Search ....................... 525/330.2, 326.9, 525/329.4; 526/320

[56] References Cited

U.S. PATENT DOCUMENTS

| | | |
|---|---|---|
| 3,264,272 | 8/1966 | Rees . |
| 3,786,116 | 1/1974 | Milkovich et al. . |
| 3,832,423 | 8/1974 | Milkovich et al. . |
| 3,842,058 | 10/1974 | Milkovich et al. . |
| 3,842,059 | 10/1974 | Milkovich et al. . |
| 3,842,146 | 10/1974 | Milkovich et al. . |
| 3,890,292 | 6/1975 | Bohme et al. ............ 526/240 |
| 3,969,434 | 7/1976 | Powell et al. . |
| 4,002,581 | 1/1977 | Dolce . |
| 4,140,115 | 2/1979 | Schonfeld . |
| 4,310,509 | 1/1982 | Berglund et al. . |
| 4,442,258 | 4/1984 | Sunakawa et al. ............ 524/767 |
| 4,499,896 | 2/1985 | Heinecke . |
| 4,554,324 | 11/1985 | Husman et al. . |
| 4,685,455 | 8/1987 | Vrouenraets . |
| 4,842,597 | 6/1989 | Brook . |
| 4,871,812 | 10/1989 | Lucast et al. . |
| 4,931,282 | 6/1990 | Asmus et al. . |
| 5,045,601 | 9/1991 | Capelli et al. . |
| 5,064,652 | 11/1991 | Bay . |
| 5,088,483 | 2/1992 | Heinecke . |
| 5,153,040 | 10/1992 | Faasse, Jr. . |
| 5,160,315 | 11/1992 | Heinecke et al. . |
| 5,183,664 | 2/1993 | Ansell . |
| 5,296,512 | 3/1994 | Beier et al. . |
| 5,380,779 | 1/1995 | D'Haese ............ 524/272 |
| 5,389,376 | 2/1995 | Duan et al. . |
| 5,395,907 | 3/1995 | Zajaczkowski . |
| 5,407,717 | 4/1995 | Lucast et al. . |
| 5,468,821 | 11/1995 | Lucast et al. . |
| 5,508,367 | 4/1996 | Zajaczkowski . |
| 5,578,683 | 11/1996 | Koch et al. ............ 525/301 |

*Primary Examiner*—Mark Nagumo

[57] ABSTRACT

An ionically-crosslinked absorbent graft copolymer which exhibits pressure sensitive adhesive properties is provided comprised of a hydrophilic and/or hydrophobic base monomer and a water-soluble or water-dispersible macromer. The ionically-crosslinked absorbent graft copolymer exhibits desirable water absorbency and water vapor transmission rates and may be used in a variety of medical applications such as a wound dressing, medical adhesive, or biomedical electrode.

26 Claims, No Drawings

IONICALLY-CROSSLINKED WATER-ABSORBENT GRAFT COPOLYMER

CROSS-REFERENCE TO RELATED APPLICATIONS

The present application is a continuation-in-part application of application Ser. No. 08/399,876, filed Mar. 7, 1995, now U.S. Pat. No. 5,508,367, which is a continuation-in-part of application Ser. No. 08/272,827, filed Jul. 11, 1994, now U.S. Pat. No. 5,395,907, issued Mar. 7, 1995.

BACKGROUND OF THE INVENTION

The present invention is directed to an ionically-crosslinked water absorbent graft copolymer.

There is an ongoing need in the medical industry for a pressure sensitive adhesive for long-term skin applications. An adhesive possessing this quality would be ideal for applications in which a patient's skin is wetted as a result of either site preparation or the accumulation of moisture under the adhesive during normal perspiration. This type of system could readily be used for surgical drapes, wound dressings, or other special applications in which durable bonding to saturated skin tissue is needed. It has been difficult to find an effective adhesive product to meet these demanding needs.

Adhesives exhibiting such properties can also be used with advantage as a biomedical electrode if made sufficiently conductive without the need to incorporate significant amounts of ionic or polar solutions into the adhesive which may result in phase separation and failure of the adhesive.

To meet the criteria described above, an adhesive must possess certain inherent qualities that are related to the chemistry of the adhesive. The design of such an adhesive should include a balance of moisture absorbent capabilities and adequate pressure sensitive adhesive properties. Hydrophilic character will enable the adhesive to interact with moisture and free up bonding sites at the adhesive/skin interface. Advantageously, not only will such an adhesive system readily absorb moisture at the skin-adhesive interface, but the adhesive will also serve as an effective vehicle to transport absorbed moisture in the form of water vapor from the adhesive to the ambient environment. This will allow for intimate contact of the adhesive with the skin.

Consideration must also be given to the safety of the adhesive. The adhesive must be non-toxic if it is to be used for medical purposes. This is especially true when bond sites are near open wounds or abrasions. An ideal long-term wound care adhesive or biomedical electrode should contain no extractables such as unreacted monomers, additives, or soluble polymeric systems. Such extractables could break down when exposed to solvents such as water. Absorption into skin, or migration to an open wound, may produce harmful effects to the patient. Therefore, it is important for the adhesive to maintain chemical integrity throughout its use.

The mechanical properties of a desirable long-term skin, wound-care or biomedical adhesive are intimately related to its composition. An ideal candidate must maintain an aggressive adhesive nature throughout its use. This includes not only the short term needs of the user, but the adhesive must be durable after long-term storage. In ambient environments, an adhesive might experience a wide range of temperature cycles over extended periods of time. Subsequent chemical changes caused by reactions, such as further crosslinking or degradation, may weaken the pressure sensitive qualities of the adhesive system.

With regard to wound dressings and biomedical electrodes, a principle form of failure is due to the delamination of the adhesive from the wound. The adhesive must exhibit sufficient water vapor transmission to avoid excessive buildup of moisture within the adhesive, as well as to encourage the removal of moisture from the interface between the adhesive and the skin.

Pressure sensitive adhesives are known which are suitable for medical purposes. See, for example, U.S. Pat. Nos. 4,140,115; 4,310,509; 4,499,896; 4,685,455; 4,842,597; 4,871,812; 4,931,282; 5,045,601; 5,064,652; 5,088,483; 5,153,040; 5,160,315; 5,183,664; 5,296,512; 5,389,376; 5,407,717; and 5,468,821.

However, a need still exists to provide a pressure sensitive adhesive which exhibits high moisture absorbency and water vapor transmission rates, minimizes skin contamination, and retains both satisfactory structural integrity and skin adhesion in the presence of significant amounts of absorbed moisture. A need also exists to enhance the electrical conductivity of such adhesive while still maintaining desirable adhesive properties.

OBJECTS AND SUMMARY OF THE PRESENT INVENTION

It is thus one object of the present invention to provide a water-absorbent graft copolymer.

It is also an object of the present invention to provide a water-absorbent pressure sensitive adhesive suitable for use as a wound dressing.

It is further an object of the present invention to provide a water-absorbent pressure sensitive adhesive suitable for use as a medical adhesive.

It is yet further an object of the present invention to provide an electrically-conductive water-absorbent pressure sensitive adhesive suitable for use as a biomedical electrode.

In accordance with the present invention, there is thus provided an ionically-crosslinked water-absorbent graft copolymer formed from one or more copolymerizable base monomers A and a water-soluble or water-dispersible macromer B, wherein said base monomer A comprises a vinyl monomer capable of forming a hydrophilic or hydrophobic polymer, and said B macromer forming polymeric sidechains of said graft copolymer, with the provisos that when said B macromer is present in an amount of at least 45 percent by weight, then at least 5 percent by weight of a monomer A having a Tg >20° C. is present, and when said B macromer is present in an amount of 35 percent by weight or less, then at least 5 percent by weight of a monomer A having a Tg <0° C. is present, and wherein ionically crosslinkable functionalities on said one or more A monomers and said B macromer are neutralized by a mono-, di- or trivalent metal ion.

In accordance with a preferred embodiment of the present invention, the graft copolymer is comprised of a water-soluble or water-dispersible macromer B comprising a hydrophilic macromer represented by the formula:

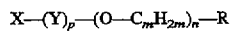

wherein X is a moiety copolymerizable with monomers A and B or capable of attachment to polymerized monomers A and B, Y is a divalent linking group, R is a terminal group; and in which m is an integer of from 2 to 6, n is an integer of from 5 to 300, and p is 0 or 1.

In accordance with another preferred embodiment of the present invention, there is provided an ionically-crosslinked pressure sensitive adhesive as described above which is ionically-crosslinked by neutralization of functionalities within the polymer backbone or the macromer sidechains to an extent sufficient to enable the crosslinked graft copolymer to be electrically conductive or to enhance the water absorbency thereof.

In accordance with the present invention, there is also provided an adhesive composite suitable for use in a medical application such as a wound dressing, medical adhesive or biomedical electrode.

DETAILED DESCRIPTION OF THE INVENTION

The ionically-crosslinked water-absorbent graft copolymer of the present invention comprises a graft copolymer of at least one copolymerizable base monomer and a hydrophilic macromer. The ionically-crosslinked graft copolymer exhibits acceptable pressure sensitive adhesive properties while retaining the ability of the copolymer to both transport moisture from the interface between the copolymer and the substrate by adsorption and to transport moisture (in the form of water vapor) through the copolymer layer to the atmosphere once absorbed.

The copolymerizable base monomer A comprises a vinyl monomer capable of forming a hydrophilic or hydrophobic polymer. Exemplary hydrophilic base monomers include hydroxy($C_{1-5}$)alkyl acrylates, hydroxy($C_{1-5}$)alkyl methacrylates, dihydroxy($C_{1-5}$)alkyl methacrylates, etc. Exemplary water-soluble base monomers include but are not limited to hydroxyethyl acrylate, hydroxypropyl acrylate, hydroxybutyl acrylate, hydroxybutyl methacrylate, as well as alkyl vinyl ethers and hydroxy alkyl vinyl ethers (wherein the alkyl group has up to 5 carbon atoms). One or more of the water-soluble A monomers may be employed.

Exemplary A monomers also include water-soluble vinyl monomers having at least one nitrogen atom. Such monomers (each of which exhibit a $T_g$ of >20° C.) include but are not limited to N-mono-substituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide, and N,N-dihydroxyethylacrylamide, etc.

Other suitable A monomers include, for example, various vinyl monomers such as acrylic and methacrylic acid, methoxyethyl acrylate or methacrylate, ethyoxyethyl acrylate or methacrylate, methyl acrylate or methacrylate, ethyl acrylate or methacrylate, propyl acrylate or methacrylate, glycerol acrylate or methacrylate, hydroxyethyl methacrylate, hydroxypropyl methacrylate, vinyl pyrrolidone and vinyl caprolactam (each of which also exhibit a $T_g$ of >20° C.). Monomeric acrylic or methacrylic acid esters of a non-tertiary alcohol having from 4–12 carbon atoms on average, and preferably from 4–8 carbon atoms, such as n-butyl acrylate or methacrylate, etc. are also suitable A monomers, with such monomers exhibiting a $T_g$ of <0° C.

The macromer B forms polymeric sidechains on the graft copolymer. The macromer B is hydrophilic by nature (i.e., the macromer is water-soluble or water-dispersible).

The macromer may be represented by the formula X—(Y)$_p$—Z—R wherein X is a moiety copolymerizable with monomers A or, in the alternative, capable of attachment to polymerized monomers A, Y is a divalent linking group, Z is a water-soluble or water-dispersible homo- or polymeric moiety essentially unreactive at copolymerization conditions, R is a terminal group, and p is 0 or 1.

More specifically, the X moiety is an unsaturated polymerizable moiety the composition of which is not critical. The X moiety may be, for example, when intended to be copolymerizable with monomers A, simply a vinyl group of the formula CHR=CR$^1$— where R is hydrogen or COOH and R$^1$ is hydrogen or alkyl such as methyl. Other exemplary X moieties include but are not limited to methacryloyl, maleoyl, itaconoyl, crotonoyl, unsaturated urethane moiety, methacrylamido and moieties of the formula CH$_2$=CHCH$_2$O—.

The X moiety may comprise an amine or alcohol moiety (such as a monohydroxyl or monoamine moiety) which permits attachment of the macromer to a suitable functionality on previously-polymerized monomers A. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A preferred Y divalent linking group is

or a linking group which incorporates such a moiety.

Additional Y linking groups which may be employed in connection with the present invention include but are not limited to the following moieties:

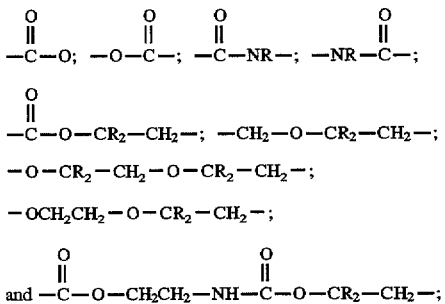

where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842,058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyvinyl caprolactam radical, polymethylvinyl ether radical or mixtures thereof. Exemplary B macromers formed from such radicals include but are not limited to ethoxylated or propoxylated hydroxy($C_{1-5}$)alkyl meth (acrylate) and polymethylvinyl ether mono(meth)acrylate.

The molecular weight of the macromer used in the present invention is not critical but will generally range from about 300 to about 50,000, and preferably from about 300 to 3,000.

The hydrophilic macromer B is more preferably represented by the formula:

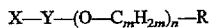

wherein X and Y are as defined above and R represents a terminal group; and in which m is an integer of from 2 to 6 and n is an integer of from 5 to 300. More specifically, macromer B is advantageously an ethoxylated or propoxylated hydroxy($C_{1-5}$)alkyl (meth)acrylate represented by the formula:

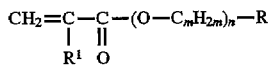

wherein $R_1$ is hydrogen or $C_{1-5}$ alkyl and R is a terminal group. Preferably, m is 2 or 3 and n is 5 to 30, and R is OH or $C_{1-5}$ alkyl.

The Z moiety is preferably comprised solely of one or more hydrophilic monomer radicals to ensure that the resulting macromer is water-soluble or water-dispersible. However, the Z moiety may also be a copolymer of hydrophilic and hydrophobic monomers, with any copolymerized hydrophobic portion being present in an amount insufficient to render the resulting macromer water-insoluble or non-water-dispersible. Desirably, any non-hydrophilic portion employed in the macromer is present in an amount of less than 50 percent by weight based on the weight of the macromer, and preferably less than 30 percent by weight.

The macromer B may employ a variety of terminal groups R. While the terminal group may typically be OH or $C_{1-5}$ alkyl, it may be desirable to select a terminal group based on the functional character of the terminal group. For instance, suitable terminal groups include but are not limited to (1) acid/ionic groups such as carboxyl, anhydride, phosphate or sulfate groups (as discussed further below), (2) hydrophobic groups such as lower alkyl, phenyl or substituted phenyl, and (3) hydrophilic groups such as hydroxyl or amine groups.

Physical properties or characteristics of the copolymer may be modified by selection of suitable terminal groups. Ionic terminal groups may be used to provide a desired degree of crosslinking; for example, by neutralizing acid moieties with metal hydroxides as discussed herein. High temperature performance may be enhanced by incorporating an acid functionality in conjunction with a ditertiary amine. Aqueous solution viscosities may be influenced by the presence of ionic terminal groups.

Preferably, said A monomer is present in an amount of from 25 to 75 percent by weight, and said B macromer is present in an amount of from 25 to 75 percent by weight, and preferably 30 to 60 percent by weight, based on the total weight of the respective components A and B in the copolymer.

By way of further proviso, when the B macromer is present in an amount of at least 45 percent by weight, it is preferred that at least 5 percent by weight of an A monomer having a $T_g$ of >20° C. is present, and when the B macromer is present in an amount of 35 percent by weight or less, it is preferred that at least 5 percent by weight of an A monomer having a $T_g$ of <0° C. is present.

The weight average molecular weight of the resulting polymer is preferably at least 18,000, and may be as high as 100,000–200,000.

As noted above, the copolymer composition of the present invention may be prepared by any conventional polymerization technique, including (1) free radical initiated copolymerization of components A in the presence of a solvent, and (2) attachment of the macromer B graft to a preformed backbone polymer formed from copolymerized monomers A via reaction with a suitable functional group on the backbone polymer subsequent to formation of same. Suitable copolymerization temperatures range from about 20° C. to about 150° C. for periods of time of from 2 to 24 hours until the desired degree of conversion occurs.

The graft copolymer of the present invention may be ionically-crosslinked in a conventional manner to provide an absorbent copolymer of enhanced properties. See, for example, the teachings of U.S. Pat. Nos. 3,264,272; 3,969,434; and 4,002,581, each herein incorporated by reference in their entirety.

The desired ionic crosslinking can occur by providing on at least a portion of the monomers A and/or macromer B functional groups which are capable of being neutralized by a mono-, di- or trivalent metal ion. Exemplary functional groups are selected from the group consisting of carboxyl, sulfate, phosphate, anhydride and mixtures thereof. For example, at least one of the copolymerizable A monomers may comprise an ionically-crosslinkable monomer such as an alpha,beta-ethlenically unsaturated carboxylic acid group having from 3–8 carbon atoms, such as acrylic acid, methacrylic acid, ethacrylic acid, itaconic acid, maleic acid, fumaric acid, monoesters and dicarboxylic acids. Alpha, beta-monoethlenically unsaturated anhydrides of carboxylic acid such as maleic anhydride can also be employed as the A monomer.

It is also possible to employ an ionically-crosslinkable macromer in addition to the ionically-crosslinkable monomer discussed above. In such an embodiment, the macromer will incorporate an acidic/ionic terminal group such as carboxyl, sulfate, phosphate, anhydride or mixtures thereof.

The amount of ionic crosslinking sites and their manner of inclusion in the graft copolymer may be varied depending upon the end result to be achieved. For example, it may be desired that a major amount of the A monomers be hydrophobic by nature in order to enhance the adhesive properties of the graft copolymer. For example, the A monomer may comprise from 3 to 10 percent by weight of acrylic or (meth)acrylic acid and the remainder a hydrophobic monomer(s). The hydrophobic monomers will normally not contain ionic crosslinking functionalities. The A monomers may be entirely hydrophobic by nature, with the water absorbency of the copolymer being nonetheless enhanced by providing for a high degree of ionic crosslinking by means of ionic crosslinkable functionalities as terminal groups on the graft macromer. In the event that all A monomers are hydrophobic by nature, it is preferred that from 50 to 100 percent of the graft macromer terminal groups consist of ionically-crosslinkable functional groups. In such an instance, the graft macromer may comprise from 35 to 75 percent by weight of the reactive mixture to maximize the number of ionically crosslinkable functionalities available for crosslinking.

As discussed in U.S. Pat. No. 3,264,272, the ionically-crosslinked graft copolymer of the present invention is produced by reaction of the copolymer with an ionizable metal compound in order to neutralize the appropriate functionalities (e.g., acid functionalities) on either the base monomers or on the macromer. Preferably, from about 2 to about 50 weight percent of the base monomers and/or the macromers contain functionalities which may be neutralized by reaction with an ionizable metal compound.

Metal ions which may be employed in the formation of the ionically-crosslinked graft copolymer include but are not limited to mono-, di- and trivalent ions of the metals of Groups I, II, III, IV and VIII. Suitable monovalent metal ions include sodium, potassium, lithium, cesium, silver, mercury and copper. Suitable divalent metal ions include beryllium, magnesium, calcium, strontium, berium, copper, cadmium, mercury, tin, lead, iron, cobalt, nickel and zinc. Suitable trivalent metal ions include aluminum, chromium, iron and yttrium. The preferred metal ions are alkali metal ions.

The crosslinking reaction (i.e., the neutralization of the appropriate neutralizable functionalities) is carried out by blending the graft copolymer with a solution of the crosslinking metal compounds in an amount sufficient to neutralize the neutralizable functionalities to the desired extent. Preferred metal compounds for use in providing the necessary neutralization include but are not limited to alkali and alkaline earth metal hydroxides. Also suitable are alkali metal salts or alkaline earth metal salts based on an organic acid, such as sodium acetate, calcium acetate, magnesium acetate, zinc formate, and zinc acetate.

The ionically-crosslinked graft copolymer exhibits highly desirable water absorption, water vapor transmission, electrical conductivity and adhesive properties and thus serves as an optimum material for a biomedical electrode.

The resulting crosslinked copolymer may be used in solution form. Preferably, the copolymer is applied to a backing material (such as a tape) in solution form, with the solvent being removed upon application to the tape. The copolymer is applied in a thickness sufficient to provide the desired adhesion together with the desired degree of water absorption. Suitable copolymer layer thicknesses range from a few microns to 5 mm or so, such as from 10 to 100 microns. Advantageously, the thickness of the layer does not affect the water vapor transmission capability of the copolymer.

Exemplary backing materials include but are not limited to flexible and inflexible backing materials conventionally employed in the area of pressure sensitive adhesives, such as creped paper, kraft paper, fabrics (knits, non-wovens, wovens), foil and synthetic polymer films such as polyethylene, polypropylene, polyvinyl chloride, poly(ethylene terephthalate) and cellulose acetate, as well as glass, ceramics, metallized polymer films and other compatible sheet or tape materials. Advantageously, the backing material is permeable to water vapor to enhance the water vapor transmission rate through the material and exhibits water absorbent properties.

The backing material may be of any desired shape and configuration, such as adhesive tapes, strips, wound dressings, surgical drapes, etc. It may be desirable to include a dressing or absorbent pad attached to the copolymer layer. Such materials may be coated in any conventional manner with the copolymer of the present invention, such as by roll coating, spray coating, extrusion coating, co-extrusion coating, hot melt coating by use of conventional coating devices. When appropriate, the copolymer of the present invention may be applied as a solution and the solvent subsequently removed to leave a tacky adhesive residue on the backing material.

The water-absorbent copolymer of the present invention may be used in a wide variety of commercial applications. For example, the crosslinked water-absorbent copolymer of the present invention may be used as a skin adhesive for adhesive tapes and bandages, as a wound dressing, as a burn dressing, as a sealant coating on catheters or other medical devices, etc. The hydrophobic/hydrophilic character of the base monomers A may be modified to enhance the applicability of the copolymer to any particular end use.

When used as a wound dressing, crosslinked graft copolymer of the present invention may include a suitable medicament such as antibacterials, antiseptics, antibiotics, nutrients, anaesthetics, analgesics, anti-inflammatories, etc. Such agents may be incorporated as a dispersed solid, in the form of a solution in admixture with the reactant monomer components prior to polymerization, or added to the crosslinked copolymer in the form of an absorbed aqueous solution (e.g., buffered or physiological saline) of the medicament. The crosslinked graft copolymer is permeable to the incorporated medicament and can thus serve as a sustained release device. Exemplary antimicrobial agents include but are not limited to iodine, chlorhexidene gluconate, parachlorometaxylenol, bacitracin salts, neomycin sulfate, silver sulfadiazine, polymyxin B sulfate, etc.

Advantageously, the crosslinked copolymer of the present invention may also be foamed to provide a highly water absorbent foamed layer for use in absorbent pads or similar articles. Such foams may be formed by conventional means, such as by adding a blowing or expanding agent to the copolymer (e.g., dichlorodifluoromethane or dichlorotetrafluoroethane) and subsequently causing the formation of a foam layer on a coated substrate of desired thickness and porosity.

Alternatively, the admixture of blowing agent and crosslinked copolymer can be injection molded to produce a molded foam article of desired shape which exhibits high water absorbency and water vapor transmission.

It is an advantage of the present invention that the crosslinked graft copolymer of the present invention exhibits a water vapor transmission rate of at least 900 grams/m$^2$/24 hours at 40° C. and at 80% relative humidity differential. Preferably, the crosslinked graft copolymer of the present invention exhibits a water vapor transmission rate of from 1000 to 4000 grams/m2/24 hours, while still exhibiting satisfactory adhesive properties.

The invention will be discussed in conjunction with the following examples, which are merely illustrative of the present invention and not intended to in any way limit the scope of the invention.

EXAMPLE 1

241.25 grams of ethyl acetate and 146.25 grams of isopropyl alcohol (as solvents) were charged to a 1-liter reaction vessel. To the charged material, 18.53% of the monomers identified below were added. Under a nitrogen atmosphere, the batch was heated to 71°–73° C. and 1.88 grams of VAZO-52 (polymerization initiator) dissolved in ethyl acetate were added. The reactants were allowed to polymerize for 20 minutes to produce a seed polymer capable of solvating the remaining reactants. The remaining 81.74% of the monomer mix along with 0.83 grams of benzoyl peroxide were added to the reaction mix over 30 minutes while maintaining a reaction temperature of 71°–73° C. The reactants were polymerized for 1 hour until all monomers were consumed. The reactor feed mix consisted of the following components:

| | Amount (Grams) |
|---|---|
| Monomers | |
| HEMA-10 (macromer) | 91.88 |
| Isooctyl Acrylate (A monomer) | 157.50 |
| Acrylic Acid (A monomer) | 13.12 |
| Solvents | |
| Ethyl acetate | 241.25 |
| Isopropyl alcohol | 146.25 |

Note: HEMA-10 is a 10 mole ethoxylate of hydroxy ethyl methacrylate (produced by BIMAX, INC.)
VAZO-52: Dupont trade name for free radical initiatoris 2,2'-azobis (2,4-dimethylpentanenitrile).

The above polymer product was ionically-crosslinked by the addition to the product of a solution of KOH/LiOH on a 1:1 weight ratio. The solution of KOH/LiOH comprised an admixture of a 20% solution of KOH in 50/50 deionized water-methanol. The solution of LiOH comprised a 16.67% solution in deionized water. For each 100 grams of polymer product (35% solids), 3.41 grams of the 20% KOH solution and 3.06 grams of the 16.67% LiOH solution are admixed with the polymer product and mixed in a Ross Mixer for 6 minutes at 1500 rpm. The addition of the KOH/LiOH solution is calculated to neutralize all of the acid functionalities in the graft copolymer with the acrylic acid monomer comprising about 5 weight percent of the total reactant mixture. The resulting ionically-crosslinked polymer product was then coated to a 1 mil thickness on Kraft K-60 S/F liner, dried at 220° F. for 7 minutes and laminated to 2 mil PET and 1 mil urethane. The MVTR of the resulting ionically-crosslinked graft copolymer was determined to be 3372 grams/m$^2$/day. The 5' peel of the graft copolymer was determined to be 64 oz.

EXAMPLE 2

The procedure of Example 1 was repeated using the following reactor feed components to produce a graft copolymer which may be similarly ionically-crosslinked to form a crosslinked absorbent copolymer:

| | Amount (Grams) |
|---|---|
| Monomers | |
| HEMA-10 (macromer) | 113.50 |
| Hydroxy Ethyl Acrylate (A monomer) | 107.38 |
| Acrylamide (A monomer) | 6.56 |
| Butyl Acrylate (A monomer) | 54.73 |
| Vinyl Pyrrolidone (A monomer) | 40.25 |
| Acrylic Acid (A monomer) | 13.12 |
| Solvents | |
| Ethyl acetate | 180.13 |
| Isopropyl alcohol | 120.09 |

EXAMPLE 3

The procedure of Example 1 was repeated using the following reactor feed components to produce a graft copolymer which may be similarly ionically-crosslinked to form a crosslinked absorbent copolymer:

| | Amount (Grams) |
|---|---|
| Monomers | |
| HEMA-10 (macromer) | 134.22 |
| Hydroxy Ethyl Acrylate (A monomer) | 97.31 |
| Hydroxy Propyl Acrylate (A monomer) | 40.27 |
| Acrylamide (A monomer) | 10.06 |
| Butyl Acrylate (A monomer) | 23.56 |
| Vinyl Pyrrolidone (A monomer) | 10.06 |
| Acrylic Acid (A monomer) | 10.06 |
| Solvents | |
| Ethyl acetate | 160.11 |
| Isopropyl alcohol | 140.11 |

EXAMPLE 4

The procedure of Example 1 was repeated using the following reactor feed components to produce a graft copolymer which may be similarly ionically-crosslinked to form a crosslinked absorbent copolymer:

| | Amount (Grams) |
|---|---|
| Monomers | |
| HEMA-10 (macromer) | 268.43 |
| Hydroxy Ethyl Acrylate (A monomer) | 181.20 |
| Hydroxy Propyl Acrylate (A monomer) | 181.20 |
| Acrylamide (A monomer) | 20.13 |
| Acrylic Acid (A monomer) | 20.13 |
| Solvents | |
| Ethyl Acetate | 345.25 |
| Isopropyl Alcohol | 255.19 |

What is claimed is:

1. An ionically-crosslinked water-absorbent graft copolymer comprising the copolymerization reaction product of one or more copolymerizable base monomers A and one or more water soluble or water dispersible macromers B, wherein said base monomers A comprise a vinyl monomer capable of forming a hydrophilic or hydrophobic polymer, and said B macromer forming polymeric sidechains on said graft copolymer and defined by the formula X—(Y)$_p$—Z—R, wherein X is a moiety copolymerizable with monomer A or capable of attachment to copolymerized monomer A, Y is a divalent linking group, Z is a water-soluble or water-dispersible homo- or copolymeric moiety, R is a terminal group, and p is 0 or 1, said macromer being present in an amount of from 30 to 75 percent by weight, based on the total weight of the respective components A and B, with the provisos that when said B macromer is present in an amount of at least 45 percent by weight, then at least 5 percent by weight of an A monomer having a Tg of >20° C. is present, and when said B macromer is present in an amount of 35 percent by weight or less, then at least 5 percent by weight of an A monomer having a Tg of <0° C. is present, and at least one of said monomers A and macromers B containing ionically crosslinkable functionalities which are neutralized by a mono-, di- or trivalent metal ion.

2. The crosslinked copolymer of claim 1 wherein said A monomer is present in an amount of from 25 to 75 percent by weight based on the total weight of the respective components A and B.

3. The crosslinked copolymer of claim 2 wherein said B macromer is present in an amount of at least 35 percent by weight.

4. The crosslinked copolymer of claim 1 wherein at least one of said A monomers has a $T_g$ of >20° C. and is hydrophilic.

5. The crosslinked copolymer of claim 1 wherein at least one of said A monomers is selected from the group consisting of hydroxy($C_{1-5}$)alkyl acrylates, hydroxy($C_{1-5}$)alkyl methacrylates, dihydroxy($C_{1-5}$)alkyl acrylates, dihydroxy ($C_{1-5}$)alkyl methacrylates and mixtures thereof.

6. The crosslinked copolymer of claim 1 wherein at least one of said A monomers is a water-soluble vinyl monomer having at least one nitrogen atom.

7. The crosslinked copolymer of claim 1, wherein said A monomer is a vinyl monomer selected from the group consisting of acrylic acid, methacrylic acid, methoxyethyl acrylate, methoxyethyl methacrylate, ethoxyethyl acrylate, ethoxyethyl methacrylate, methyl acrylate, methyl methacrylate, ethyl acrylate, ethyl methacrylate, propyl acrylate, propyl methacrylate, n-butyl acrylate, n-butyl methacrylate, vinyl pyrrolidone, vinyl caprolactam and mixtures thereof.

8. The crosslinked copolymer of claim 1 wherein X is a (meth)acrylate moiety.

9. The crosslinked copolymer of claim 1 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

10. The crosslinked copolymer of claim 1 wherein said macromer is defined by the formula:

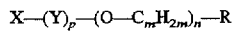

wherein X is a moiety copolymerizable with monomers A or capable of attachment to copolymerized monomers A, Y is a divalent linking group, R is a terminal group, m is an integer of from 2 to 6, n is an integer of from 5 to 300, and p is 0 or 1.

11. The crosslinked copolymer of claim 10 wherein the macromer is defined by the formula

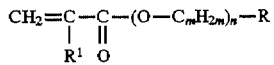

wherein $R_1$ is hydrogen or $C_{1-5}$ alkyl and R is a terminal group.

12. The crosslinked copolymer of claim 11 wherein R is selected from the group consisting of carboxyl, sulfate, phosphate, anhydride, hydroxyl and $C_{1-5}$ alkyl.

13. The crosslinked copolymer of claim 11 wherein n is an integer of from 5 to 30.

14. The crosslinked copolymer of claim 1 wherein said macromer is selected from the group consisting of ethoxylated hydroxyethyl (meth)acrylate and ethoxylated hydroxypropyl (meth)acrylate.

15. The crosslinked copolymer of claim 1 wherein said macromer is selected from the group consisting of ethoxylated hydroxy ($C_{1-5}$ alkyl) acrylate, propoxylated hydroxy ($C_{1-5}$ alkyl) acrylate, ethoxylated hydroxy ($C_{1-5}$ alkyl) methacrylate and propoxylated ($C_{1-5}$ alkyl) methacrylate.

16. The crosslinked copolymer of claim 1 wherein said macromer is selected from the group consisting of ethoxylated and propoxylated hydroxy ($C_{1-5}$ alkyl) (meth)acrylate, poly(2-ethyl-2-oxazoline), polyacrylic acid, polyvinyl alcohol, polyvinyl pyrrolidone, polyvinyl caprolactam and polymethylvinyl ether mono (meth)acrylate.

17. The crosslinked copolymer of claim 1 wherein at least a portion of said base monomers A include a functionality which is neutralized by a mono-, di- or trivalent metal ion.

18. The crosslinked copolymer of claim 17 wherein said functionality is selected from the group consisting of carboxyl, sulfate, phosphate, anhydride and mixtures thereof.

19. The crosslinked copolymer of claim 17 wherein from about 50 to about 100 percent of said functionalities are neutralized.

20. The crosslinked copolymer of claim 17 wherein said A monomer comprises acrylic or (meth)acrylic acid in an amount ranging from about 3 to about 10 percent by weight based on the total weight of components A and B.

21. The crosslinked copolymer of claim 1 wherein at least a portion of said macromer B includes terminal groups which are neutralized by a mono-, di- or trivalent metal ion.

22. The crosslinked copolymer of claim 21 wherein said terminal groups which are neutralized are selected from the group consisting of carboxyl, sulfate, phosphate, anhydride and mixtures thereof.

23. The crosslinked copolymer of claim 1 wherein at least a portion of both said monomers A and said macromer B include functionalities which are neutralized by a mono-, di- or trivalent metal ion.

24. The crosslinked copolymer of claim 1 wherein both said A monomer and said B macromer contain ionically crosslinkable functionalities which are neutralized by a mono-, di- or trivalent metal ion.

25. The crosslinked copolymer of claim 24 wherein said functionalities are selected from the group consisting of carboxyl, sulfate, phosphate, anhydride and mixtures thereof.

26. The crosslinked copolymer of claim 24 wherein from about 50 to about 100 percent of said functionalities are neutralized.

* * * * *